United States Patent [19]

Yunoki et al.

[11] Patent Number: 4,686,964
[45] Date of Patent: Aug. 18, 1987

[54] ENDOSCOPE PICKUP MEANS

[75] Inventors: Yutaka Yunoki, Kunitachi; Tatsuo Nagasaki, Musashino, both of Japan

[73] Assignee: Olympus Optical Co., Ltd., Tokyo, Japan

[21] Appl. No.: 830,248

[22] Filed: Feb. 18, 1986

Related U.S. Application Data

[63] Continuation of Ser. No. 559,112, Dec. 7, 1983, abandoned.

[30] Foreign Application Priority Data

Dec. 7, 1982 [JP] Japan ................. 57-214229

[51] Int. Cl.[4] .................... A61B 1/04; A61B 1/06
[52] U.S. Cl. ............................................ 128/4; 128/6
[58] Field of Search ........................... 128/4-9, 128/804, 902; 200/154 B, 305; 340/365 C; 455/300, 301

[56] References Cited

U.S. PATENT DOCUMENTS

| | | | |
|---|---|---|---|
| 1,019,236 | 3/1912 | Fessenden | 455/300 |
| 3,279,460 | 12/1961 | Sheldon | 128/6 |
| 3,317,698 | 5/1967 | Mansfield | 200/305 |
| 3,542,988 | 11/1970 | Baldasare | 200/305 |
| 3,959,617 | 5/1976 | Hults | 200/305 |
| 3,987,263 | 10/1976 | Ogasawara | 200/305 |
| 4,240,443 | 12/1980 | Ionescu | 128/902 |
| 4,245,649 | 1/1981 | Schmidt-Andersen | 128/804 |
| 4,264,903 | 4/1981 | Bigelow | 340/365 C |
| 4,473,841 | 9/1984 | Murakoshi et al. | 128/6 |

Primary Examiner—Lee S. Cohen
Assistant Examiner—David Shay
Attorney, Agent, or Firm—Armstrong, Nikaido, Marmelstein & Kubovcik

[57] ABSTRACT

Electromagnetic shield means are provided on the optical axis of the detector end of an endoscope incorporating pickup means for providing an optical image and converting the image photoelectrically. The electromagnetic shield means are mounted at the preceding end of the endoscopic pickup means for preventing external electromagnetic effects so as to provide distinct image pickup of an object to be examined.

8 Claims, 6 Drawing Figures

FIG. 4
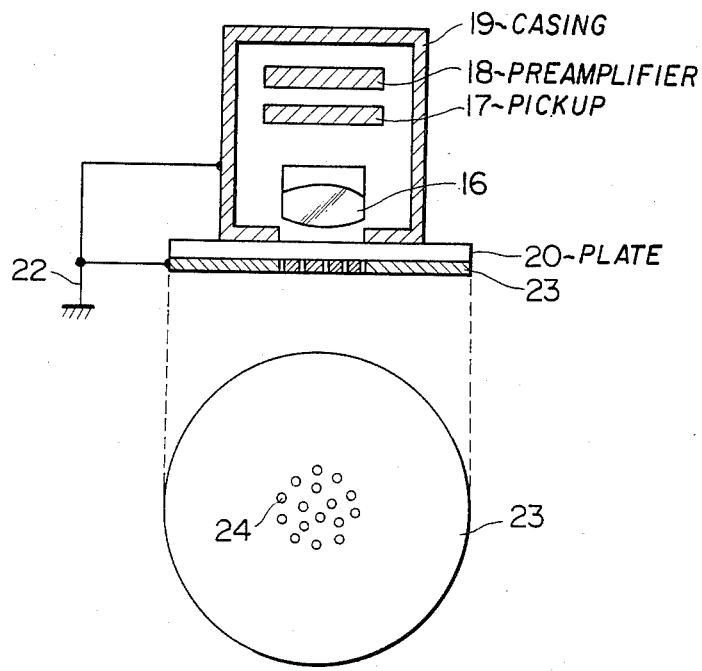
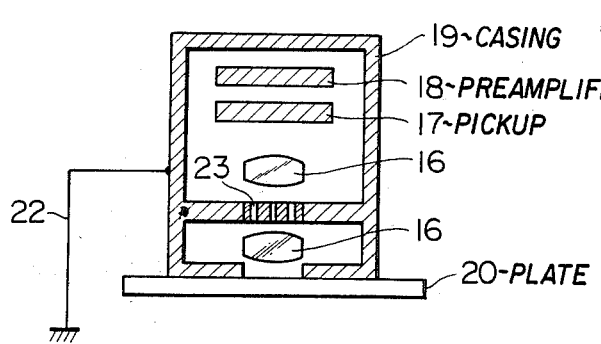
FIG. 5(a)
FIG. 5(b)
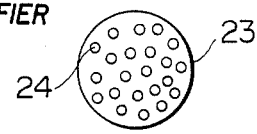

ENDOSCOPE PICKUP MEANS

This application is a continuation of application Ser. No. 559,112 filed Dec. 7, 1983, now abandoned.

BACKGROUND OF THE INVENTION

The present invention relates to endoscopic pickup means incorporating pickup members to be inserted into the inside of an object to be examined and acting to provide an optical image at that portion and to convert the image photoelectrically. It relates also to an endoscopic pickup means equipped with an electromagnetic shield for preventing external electrical or magnetic effects on the pickup members in the pickup means.

Recently, there have been widely available endoscopic pickup means for observing the inside of an object to be examined by inserting the distal end thereof into the inside of the object. Such known endoscopic pickup means include those endoscopes equipped at a tip portion thereof with a pickup members for providing an optical image and for converting the image photoelectrically. The distal end portion acts as a detector end as shown in a prior art embodiment in FIG. 1 as follows:

A ultrasonic scanner 1, pickup means 2 and photoconductive fibre tube 3 are installed in a container 4 at the distal end portion to pickup an ultrasonic tomographic and optical image of the object. Such pickup means 2 are composed of an optical lens 6, solid state image pickup element 7 and preamplifier 8 and are installed in a container defined by electromagnetic shield casing 9 and lead glass plate 10. Such endoscopic pickup means are used frequently together with various other means. For example, the means are used together with an electric knife for surgical operations. Such an electric knife uses a high frequency electric current of from 500 Khz to 5 MHz and consumes power from 50 to 300 W under a source voltage of from 1,000 to 1,200 V. When the endoscopic pickup means are used in combination with an electric knife supplied with a high frequency current, the high frequency current flows into the pickup means even in the presence of minor electrostatic capacity of such a means. Although the pickup means 2 prevents external electric or magnetic effects by means of the container 4 and electromagnetic shield casing 9 in the detector end, as shown in FIG. 1, such shielding is only effective with respect to the side or back side of the solid state image pickup element 7 in the pickup means 2 but is ineffective with respect to the direction of optical lens, i.e. with respect to the optical axis. Hence, when an electric knife and endoscopic pickup means are used together, noise emanating from the electric knife may often interfere detrimentally with the functioning of the detector end of the endoscopic pickup means and may even damage the semiconductors such as the solid state image pickup element 7 incorporated in the endoscopic pickup means. In particular, when the electrodes of the electric knife and solid state image pickup element 7 coexist in the same endoscopic pickup means, both should be isolated or shielded completely. The use of solid state image pickup element 7, i.e. optical pickup means, necessitates an optical passage for passing light. Such an optical passage should be shielded sufficiently.

BRIEF SUMMARY OF THE INVENTION

The present invention is directed to eliminating such disadvantages. It is thus a primary object of the present invention to provide an endoscopic imaging pickup means capable of preventing electric problems due to the electromagnetic effects thereon in cases of combined use therewith of other means such as an electric knife, in order to effect distinct image pickup of an object to be examined.

Other features and advantages achieved by the present invention will be made apparent by the following description.

BRIEF DESCRIPTION OF THE DRAWINGS

FIGS. 2 and 3 relate to a first embodiment of the present invention, wherein FIG. 2 is a structural drawing of the detector end of an endoscope according to the first embodiment and FIG. 3 is a sectional view of electromagnetic shielding means at the detector end according to the first embodiment.

FIG. 4 relates to a second embodiment of the present invention and illustrates a sectional view of electromagnetic shielding means at the detector end of an endoscopic pickup means.

FIGS. 5(a) and 5(b) illustrate sectional views of the detector end of an endoscopic pickup means according to a third embodiment of the present invention.

DETAILED DESCRIPTION OF THE EMBODIMENTS

Figure 1:
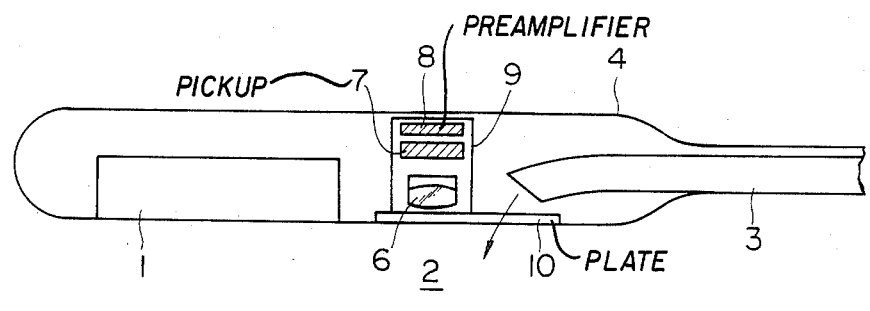
FIG. 1 is a structural drawing of the detector end of a prior art endoscopic pickup means.
Figure 1:
Figure 2:
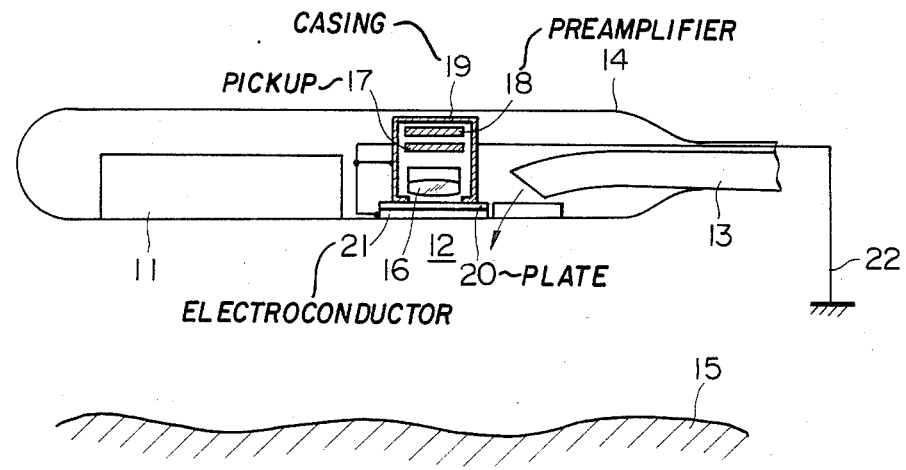
Figure 3:
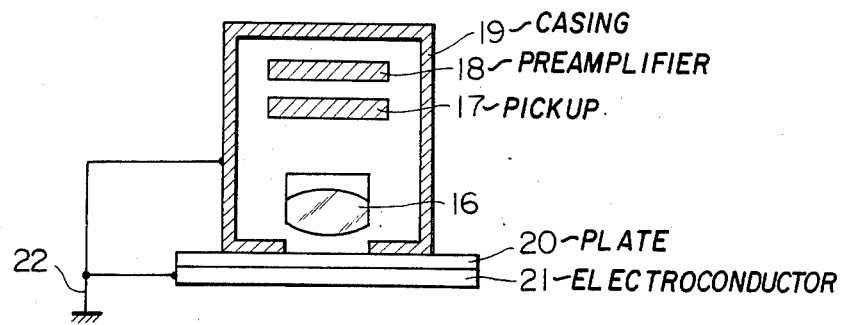

Here will be disclosed the first embodiment of the present invention with reference to FIGS. 2 and 3.

As shown in FIGS. 2 and 3, ultrasonic scanner 11, pickup means 12 and photoconductive fibre tube 13 are installed in a tip container 14 at the detector end of an endoscopic pickup means to effect the optical pickup and ultrasonic tomography of an object 15 to be examined. The pickup means 12 are composed of an optical lens 16, solid state image pickup element 17 and preamplifier 18 and are installed in a container defined by an electromagnetic shield casing 19 and lead glass plate 20. The lead glass plate is lined with a transparent electroconductor 21 formed from tin oxide and the electromagnetic shield casing 19 and transparent electroconductor 21 are grounded through a ground bar 22.

In the detector end of the present means incorporating such a pickup means 12, due to (a) the installation of pickup means 12 in an enclosed container defined by the electromagnetic shield casing 19 and the transparent conductor 21 and (b) due to the potential drop at the electromagnetic shield casing 19 and transparent conductor plate 21 to the ground potential, the electromagnetic noise is grounded from the electromagnetic shield casing 19 and transparent electroconductor 21 through the ground bar 22 in the combined use of the pickup means 12 and any means which emits electromagnetic noise such as an electric knife, thereby performing the imaging pickup of the object 15 without being affected by such electromagnetic noise. In particular, electromagnetic noise from the optical axis is shielded by the transparent conductor plate 21. As the transparent electroconductor plate 21 is made of optically transparent material, it does not have an affect on the optical pickup system.

The second and third embodiments will be now set forth with reference to FIGS. 4, 5(a) and 5(b). In order to omit further description of such details, the same parts as those in FIGS. 2 and 3 are designated with the same reference numerals.

FIG. 4 is a sectional view of the second embodiment. The electromagnetic shield means as shown in FIG. 4 is formed by bonding an electromagnetic shield net 23 made by forming Permalloy into a parallel plate with the transparent electroconductor plate 21 for the electromagnetic shielding means as shown in FIGS. 2 and 3. The electromagnetic shield net 23 is provided with a great number of optical perforations 24 at the zone intersecting with the optical axis of the optical lens 16 and solid state image pickup element 17.

FIGS. 5(a) and 5(b) are sectional views of the third embodiment. The electromagnetic shield means is comprised by providing electromagnetic shield net 23 as shown in FIGS. 4 and providing optical perforations 24 over the zone thereof equivalent to the effective diameter of the flux of light at the pupil position of the optical lens members therebetween. This optical perforation zone 24 of electromagnetic shield net 23 is designed so that the modulation transfer function (MTF) of the optical lens is reduced only within a spatial frequency higher than the resolving power of solid state image pickup element 17.

Modification of the electromagnetic shield means as in the second and third embodiments can prevent the external electromagnetic effects as in the first embodiment.

In addition, the electromagnetic shield net 23 may be prepared by laminating a Permalloy plate and another metal plate such as a lead plate and providing therethrough a great number of optical perforations, providing the shield plate with X ray-shielding effectiveness.

Accordingly, the present invention provides an endoscopic pickup means capable of providing a distinct image of an object to be examined without electric trouble in the combined use of a means emitting electromagnetic noise such an as electric knife, by installing the solid state image pickup means in a container defined by a shield casing and a transparent electroconductor plate and optionally an electromagnetic shield net, and grounding the container.

It is apparent that various embodiments and modifications can be made widely without departing from the spirit and scope of this invention. Accordingly, the present invention should not be restricted to any particular embodiments except the items as claimed in the attached claims.

What is claimed is:

1. An endoscope optical pickup means comprising: a tip probe insertable into an object to be examined, endoscope optical image pickup means disposed in a detector end of said tip probe for providing an optical image of the interior of an object to be examined and for photoelectrically converting said optical image, said endoscope optical image pickup means being installed in an electromagnetic shield casing in said detector end of said tip probe and provided with optically transparent electromagnetic shield means installed in front of said optical image pickup means and across an optical axis of said endoscopic optical image pickup means, said electromagnetic shield casing and said optically transparent electromagnetic shield means being electrically connected with each other, said electromagnetic shield casing and said optically transparent electromagnetic shielding means being connected to a ground potential for shielding said endoscopic optical image pickup means from external electromagnetic noise, said optically transparent electromagnetic shield means comprising a light transmitting member and an optically transparent electroconductive member laminated to said light transmitting member for shielding said optical image pickup means from external electromagnetic noise with respect to said optical axis of said endoscope optical image pickup means.

2. Endoscopic optical image pickup means in accordance with claim 1, wherein said optically transparent electromagnetic shield means further comprises electromagnetic shield net means of a material having high magnetic permeability, said electromagnetic shield net means being formed as a plate bonded parallel with said transparent electroconductive member and provided with a plurality of optical perforations therethrough at a zone thereof extending across said optical axis of said endoscopic optical image pickup means.

3. Endoscopic optical image pickup means in accordance with claim 1 further comprising a pair of optical lens members disposed on said optical axis thereof, wherein said optically transparent electromagnetic shield means comprises electromagnetic shield net means extending across said optical axis of said endoscopic optical imaging means and between said pair of optical lens members, said electromagnetic shield net means being formed of a material having high magnetic permeability and provided with a plurality of optical perforations therethrough over a zone thereof equivalent to the effective diameter of the flux of light at a pupil position of said pair of optical lens members.

4. Endoscopic optical image pickup means in accordance with claim 3 wherein said electromagnetic shield net means are provided at the pupil position of said pair of optical lens members.

5. Endoscopic optical image pickup means installed at a tip probe of a detector end of an endoscope insetable into an object to be examined for providing optical pickup of an interior image of said object and photoelectrically converting said optical image, comprising:

optical lens means having an optical axis, for forming an optical image;

solid state optical image pickup means installed on said optical axis of said optical lens means for photoelectrically converting said optical image formed by said optical lens means into an electrical image signal;

amplifier means for amplifying said electrical image signal;

an electromagnetic shield casing partially enclosing said optical lens means, solid state optical image pickup means and amplifier means;

a light transmitting member extending in front of said optical lens means and extending across said optical axis of said optical lens means, said light transmitting member cooperating with said electromagnetic shield casing and completely enclosing said optical lens means, solid state optical image pickup means and amplifier means; and optically transparent electroconductor means lining said light transmitting member and extending across said optical axis of said optical lens means, said optically transparent electroconductor means being electrically connected to said electromagnetic shield casing, said optically transparent electroconductor means providing shielding from external electromagnetic noise with respect to said optical axis of said optical lens means;

wherein said electromagnetic shield casing and said optically transparent electroconductor means being electrically connected to a ground potential for shielding said solid state optical image pickup means and said amplifier means from external electromagnetic noise 6. Endoscopic optical image pickup means in accordance with claim 5, further comprising electromagnetic shield net means of a material having high magnetic permeability, said electromagnetic shield net means being formed as a plate parallel bonded with said optically transparent electroconductor means and provided with a plurality of perforations therethrough at a zone thereof extending across said optical axis of said optical lens means and said solid state optical image pickup means, for shielding said solid state optical image pickup means and said amplifier means from external electromagnetic noise with respect to said optical axis.

7. Endoscopic optical image pickup means installed at a tip probe of a detector end of an endoscope insertable into an object to be examined for providing optical pickup of an interior image of said object and photoelectrically converting said optical image, comprising:
- a pair of optical lens members having a common optical axis, for forming an optical image;
- solid state optical image pickup means installed on said optical axis of said pair of optical lens members for photoelectrically converting said optical image formed by said pair of optical lens members into an electrical image signal;
- amplifier means for amplifying said electrical image signal;
- an electromagnetic shield casing partially enclosing said pair of optical lens members, solid state optical image pickup means and amplifier means, said electromagnetic shield casing being connected to a ground potential for shielding said solid state optical image pickup means and said amplifier means from external electromagnetic noise;
- a light transmitting member extending across said optical axis of said pair of optical lens members and in cooperation with said electromagnetic shield casing completely enclosing said pair of optical lens members, solid state optical image pickup means and amplifier means; and
- electromagnetic shield net means for reducing the modulation transfer function of said pair of optical lens members only within a spatial frequency higher than a resolving power of said solid state optical image pickup means, said electromagnetic shield net means shielding said solid state optical image pickup means and said amplifier means from external electromagnetic noise with respect to said optical axis of said pair of optical lens members and said solid state optical image pickup means, said electromagnetic shield net means being mounted in said electromagnetic shield casing so as to extend across said optical axis of said pair of optical lens members and said solid state optical image pickup means and between said pair of optical lens members and formed of a material having high magnetic permeability, said electromagnetic shield net means being provided with a plurality of optical perforations therethrough over a zone thereof equivalent to the effective diameter of the flux of light at a pupil position of said pair of optical lens members.

8. Endoscopic optical image pickup means in accordance with claim 7, wherein said electromagnetic shield net means are provided on said focal plane of said pair of optical lens members.

* * * * *